(12) United States Patent
Summerton et al.

(10) Patent No.: US 6,635,179 B1
(45) Date of Patent: *Oct. 21, 2003

(54) STERILE FLUID FILTRATION CARTRIDGE AND METHOD FOR USING SAME

(75) Inventors: James Summerton, Park Ridge, NJ (US); Gregory R. Collins, Monroe, NY (US)

(73) Assignee: Nephros, Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/477,081

(22) Filed: Dec. 30, 1999

(51) Int. Cl.$^7$ .............................................. B01D 61/00
(52) U.S. Cl. .............. 210/650; 210/321.8; 210/321.81; 210/321.9
(58) Field of Search .................. 210/321.8, 321.79, 210/321.81, 321.9, 650, 645, 651, 96.2

(56) References Cited

U.S. PATENT DOCUMENTS

| | | | |
|---|---|---|---|
| 3,579,441 A | 5/1971 | Brown | |
| 3,878,095 A | 4/1975 | Frasier et al. | 210/87 |
| 3,946,731 A | 3/1976 | Lichtenstein | 128/214 |
| 3,976,576 A | 8/1976 | Jacobsen et al. | 210/321 |
| 4,038,190 A | 7/1977 | Baudet et al. | 210/321 B |
| 4,056,467 A | 11/1977 | Christen et al. | |
| 4,118,314 A | 10/1978 | Yoshida | 210/22 |
| 4,134,834 A | 1/1979 | Brous | 210/127 |
| 4,141,835 A * | 2/1979 | Schael et al. | |
| 4,219,422 A | 8/1980 | Knothe et al. | 210/137 |
| 4,289,623 A * | 9/1981 | Lee | |
| RE31,029 E * | 9/1982 | Schael | |
| 4,381,999 A | 5/1983 | Boucher et al. | 210/637 |
| 4,468,329 A | 8/1984 | Shaldon | 210/210 |
| 4,498,990 A | 2/1985 | Shaldon et al. | 210/637 |
| 4,647,378 A | 3/1987 | Minami | 210/646 |
| 4,702,829 A | 10/1987 | Polaschegg et al. | 210/195.2 |
| 4,708,802 A | 11/1987 | Rath et al. | 210/641 |

(List continued on next page.)

FOREIGN PATENT DOCUMENTS

| | | | |
|---|---|---|---|
| EP | 0 018 734 | 11/1980 | B01D/13/00 |
| EP | 0 076 422 | 4/1983 | A61M/1/03 |
| EP | 0 890 368 | 1/1999 | A61M/1/16 |
| WO | WO 92/11878 | 7/1992 | A61M/1/00 |
| WO | WO 98/16171 | 4/1998 | A61F/2/02 |
| WO | WO 98 30258 | 7/1998 | |
| WO | 98/50090 | 11/1998 | A61M/1/14 |
| WO | 00/44478 | 8/2000 | B01D/63/02 |

OTHER PUBLICATIONS

Polaschegg, Hans–Dietrich et al.: Hemodialysis Machines and Monitors, Hemofiltration and hemodiafiltration pp. 354–356.
Ronco, C. et al.: Technical and Clinical Evaluation of Different Short, Highly Efficient Dialysis Techniques. Contr. Nephrol., vo. 61, pp. 46–68 (Karger, Basel 1988).
Shinaberger, James H. et al.: 16: Short Treatment, Techniques for shortened treatment pp. 372–375.

*Primary Examiner*—Ana Fortuna
(74) *Attorney, Agent, or Firm*—Darby & Darby

(57) ABSTRACT

A filtration assembly is presented which removes bacteria and endotoxin from a solution so that a sterile fluid is produced. The sterile fluid is suitable for direct on-line infusion to a patient from a device, such as a dialysis machine. The filtration assembly is constructed so that two separate filtration compartments exist, resulting in redundant filtration of the fluid prior to infusion. Each compartment holds a filter which preferably consists of a longitudinal bundle of semipermeable hollow fibers. The filter is sized so that it creates a separate area within the compartment for filtrate and infusate flow. This redundant filtration produces a lower risk of creating a pyrogenic or septic condition in the patient due to filter failure.

37 Claims, 2 Drawing Sheets

U.S. PATENT DOCUMENTS

| | | | |
|---|---|---|---|
| 4,732,673 A | * 3/1988 | Dagard et al. | |
| 4,770,769 A | 9/1988 | Schael | 210/96.2 |
| 4,784,768 A | * 11/1988 | Matheieu | |
| 4,834,888 A | 5/1989 | Polaschegg | 210/646 |
| 4,861,485 A | 8/1989 | Fecondini | 210/641 |
| 4,917,798 A | * 4/1990 | Liou et al. | |
| 4,929,259 A | * 5/1990 | Caskey et al. | |
| 5,011,607 A | 4/1991 | Shinzato | 210/637 |
| 5,013,437 A | * 5/1991 | Trimmer et al. | |
| 5,069,788 A | * 12/1991 | Radovich et al. | |
| 5,075,003 A | 12/1991 | Aoyagi | 210/321.8 |
| 5,176,725 A | * 1/1993 | Puri et al. | |
| 5,178,763 A | 1/1993 | Delaunay | 210/644 |
| 5,194,157 A | 3/1993 | Ghezzi et al. | 210/646 |
| 5,238,561 A | * 8/1993 | Sanda et al. | |
| 5,244,568 A | 9/1993 | Lindsay et al. | 210/87 |
| 5,282,964 A | * 2/1994 | Young et al. | |
| 5,431,811 A | 7/1995 | Tusini et al. | 210/90 |
| 5,476,592 A | 12/1995 | Simard | 210/651 |
| 5,487,827 A | 1/1996 | Peterson et al. | 210/87 |
| 5,660,722 A | 8/1997 | Nederlof | 210/90 |
| 5,660,772 A | 8/1997 | Nederlof | 210/321.65 |
| 5,690,831 A | 11/1997 | Kenley et al. | 210/646 |
| 5,700,372 A | 12/1997 | Takesawa et al. | 210/321.81 |
| 5,725,775 A | 3/1998 | Bene et al. | 210/646 |
| 5,744,042 A | 4/1998 | Stange et al. | 210/645 |
| 5,808,181 A | 9/1998 | Wamsiedler et al. | 73/38 |
| 5,882,516 A | 3/1999 | Gross et al. | 210/321.6 |
| 5,942,112 A | 8/1999 | Ishak | 210/321.6 |
| 6,315,895 B1 | * 11/2001 | Summerton et al. | 210/96.2 |

* cited by examiner

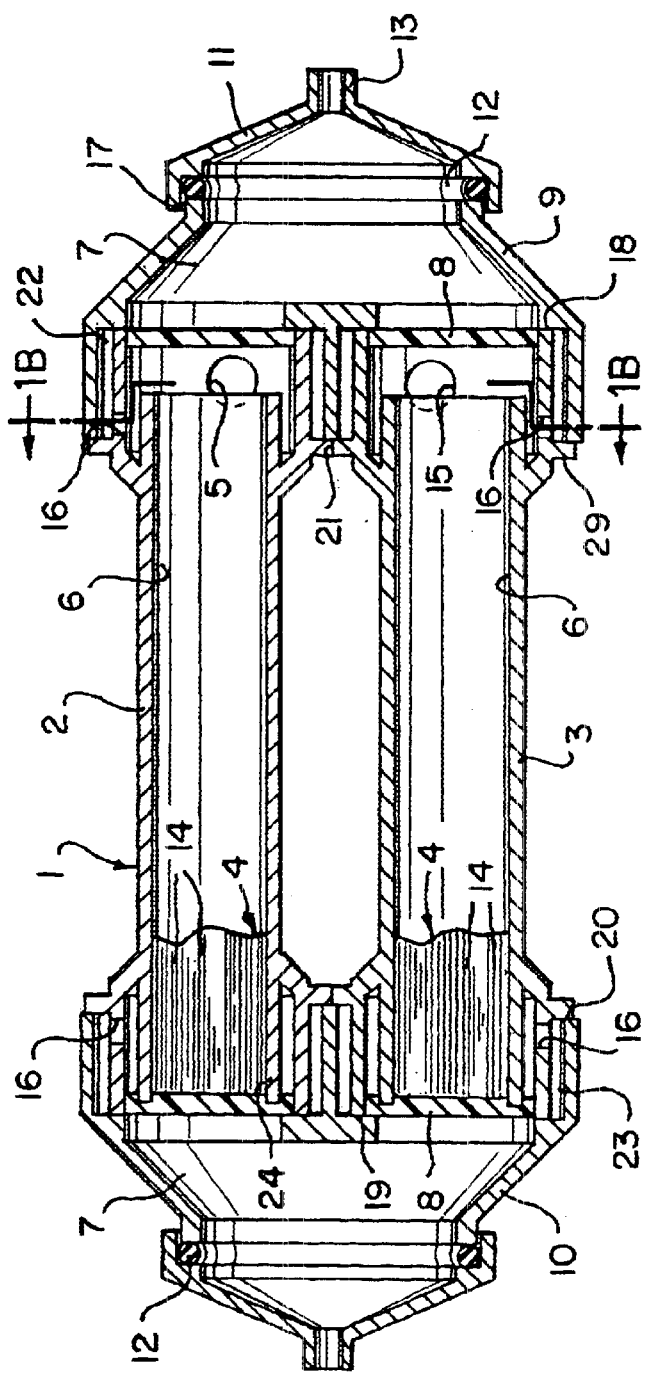
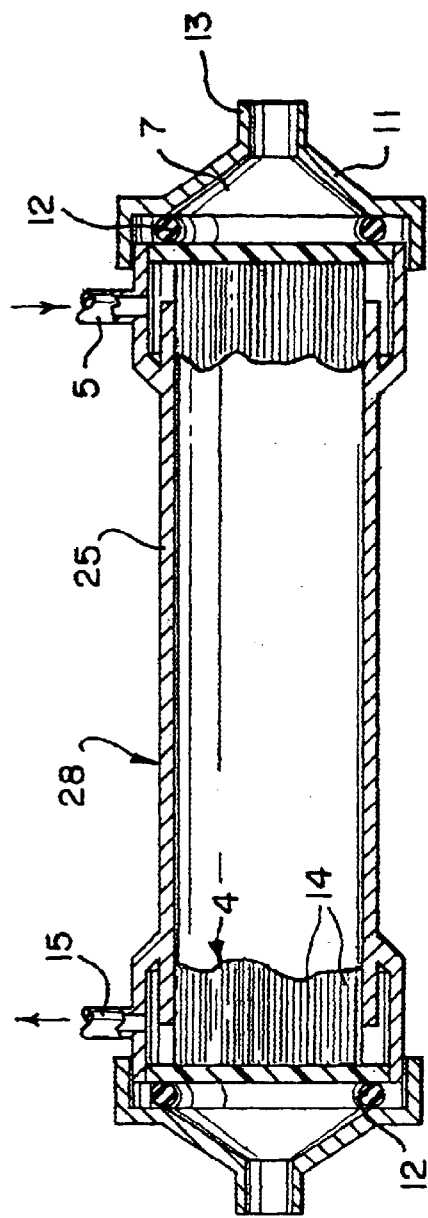
FIG. 1A
FIG. 2A

STERILE FLUID FILTRATION CARTRIDGE AND METHOD FOR USING SAME

FIELD OF THE INVENTION

This invention relates to an apparatus and method for disinfecting and sterilizing, and relates more particularly to an apparatus and method with filtering means for providing sterile infusion fluid.

BACKGROUND OF THE INVENTION

In general, patients who require certain medications, re-hydration, blood replenishment, nutritional supplements, and the like, receive appropriate sterile fluids by infusion directly into the patient's bloodstream. This is typically accomplished through use of an intravenous (IV) bag connected via a plastic tubing to a needle with is inserted into a patient's vein or artery. IV bags usually provide from one to two liters of sterile fluid before their supply is spent, after which a new IV bag must be provided. Changing IV bags can be a time-consuming process. Thus, IV infusion may work well for slow infusion rate and/or small volume procedures. However for certain procedures which require large volumes and/or rapid supplies of fluid, such as providing replacement fluid for hemofiltration and providing transfer fluid for peritoneal dialysis, infusion using IV bags is not desirable.

Instead, with hemofiltration, non-sterile fluid is filtered through one or a series of filtering devices and then infused directly into the patient's bloodstream. The filtered fluid may be a patient ultrafiltrate or a non-sterile substitution fluid received from an outside source, so as to minimize a patient's fluid loss. In any event, to accomplish filtration with minimal risk to the patient, the filter arrangement used in the process must remove endotoxins, bacteria and other pyrogen-inducing compounds. If a filter should fail during the process, a patient may suffer a septic or pyrogenic reaction due to inadequately filtered fluid.

Several filtration techniques and devices currently exist for hemofiltration and dialysis. Online production of substitution fluid is described, for example, in D. Limido et al., "Clinical Evaluation of AK-100 ULTRA for Predilution HF with On-Line Prepared Bicarbonate Substitution Fluid. Comparison with HD and Acetate Postdilution HF", *International Journal of Artificial Organs*, Vol. 20, No.3 (1997), pp. 153–157. Hemodiafiltration schemes using a single dialyzer cartridge containing a high flux semi-permeable membrane are described in P. Ahrenholz et al., "On-Line Hemodiafiltration with Pre- and Postdilution: A comparison of Efficiency", *International Journal of Artificial Organs*, Vol. 20, No.2 (1997), pp 81–90 ("Ahrenholz et al."). A hemodiafiltration scheme using first and second dialyzer cartridges is described in J. H. Miller et al., "Technical Aspects of High-Flux Hemodiafiltration for Adequate Short (Under 2 Hours) Treatment", *Transactions of American Society of Artificial Internal Organs* (1984), pp. 377–380.

These and other prior art schemes for online filtration ultimately rely on a single filter as the final barrier between contaminated and sterile fluid supplies for infusion. A failure in this final barrier could be fatal or life-threatening. A particular danger lies in dialyzer schemes which rely on back-filtration of blood, since some pyrogen-inducing substances containing endotoxin fragments have been shown to pass through the single filter during the procedure. See, for example, R. Bigazzi, et al., "High-Permeable Membranes and Hypersensitivity-like Reactions: Role of Dialysis Fluid Contamination", *Blood Purification*, Vol. 8, No. 4 (1990), pp. 190–198 and N. Hosoya, et al., "Back Diffusion Rather than Back Filtration Enhances Endotoxin Transport Through Highly Permeable Dialysis Membranes", *ASAIO Transactions*, Vol 36, No. 3 (1990), pp. M311–313.

Therefore, there is a need to provide a redundant, stand-alone sterile fluid filter that can be used with any machine or method that produces phyisiologic fluid, preferably in large volumes, which is suitable for patient infusion. There is a further need for a stand-alone filter that can be used with large volume and/or rapid flow procedures.

SUMMARY OF THE INVENTION

In order to address the shortcomings of the prior art, a first embodiment of the instant invention includes a filtration assembly comprising: (1) a first sterilization stage including an inlet port for receiving a fluid into the filtration assembly, the first sterilization stage further including at least one first stage outlet; (2) a second sterilization stage including an outlet port for expelling the fluid from the filtration assembly after filtration, the second sterilization stage having at least one second stage inlet; and (3) a stage connector fixedly attached between the first and second stages and allowing communication of the fluid between the first stage outlet and the second stage inlet.

A second embodiment of the instant invention includes a method for filtering a fluid comprising the steps of: (1) receiving a fluid at an inlet port of a casing; (2) transporting the fluid to a first filter within the casing; (3) filtering the fluid through an outer portion of the first filter; (4) expelling the fluid through an end of the first filter to an interstage connector; (5) receiving the fluid from the interstage connector at an end of a second filter; (6) filtering the fluid from the end of the second filter to an outer portion of the second filter; (7) expelling the fluid from the outer portion of the second filter; and (8) receiving the fluid at an outlet port for infusion to a patient.

A third embodiment of the instant invention includes a filtration assembly comprising: (1) a casing; (2) a separating rib for dividing the casing into a first portion for enclosing a first filter and a second portion for enclosing a second filter, the separating rib further for preventing direct fluid communication between the first and second portions; (3) an inlet port in fluid communication with the first filter; (4) an outlet port in fluid communication with the second filter; and (5) at least one interstage portion for providing fluid communication between an end of the first filter and an end of the second filter.

It is contemplated that the dual filtration assembly of the present invention may be manufactured in sections, each comprising a separate casing for later attachment. It is further contemplated that the dual filtration assembly may be manufactured such that both casings are provided simultaneously. It is additionally contemplated that a single, large casing may be provided with separate filtration compartments for accomplishing redundant filtration.

An advantage of the instant invention is that a redundant filtration system for producing infusate for a patient is provided in which the chance of septic and/or pyrogenic reactions occurring due to a failure of one filter is decreased. Systems of the prior art do not provide for such redundant protection.

BRIEF DESCRIPTION OF THE DRAWINGS

Further objects and advantages of the present invention will become apparent to one of ordinary skill in the art upon review of the following detailed description of preferred embodiments when taken in conjunction with the accompanying drawings, of which:

FIG. 1A is a cross-sectional top view of a first filtration assembly according to the first embodiment;

FIG. 2A is a cross-sectional top view of a second filtration assembly according to a second embodiment;

DETAILED DESCRIPTION OF THE PREFERRED EMBODIMENTS

Figure 1B:
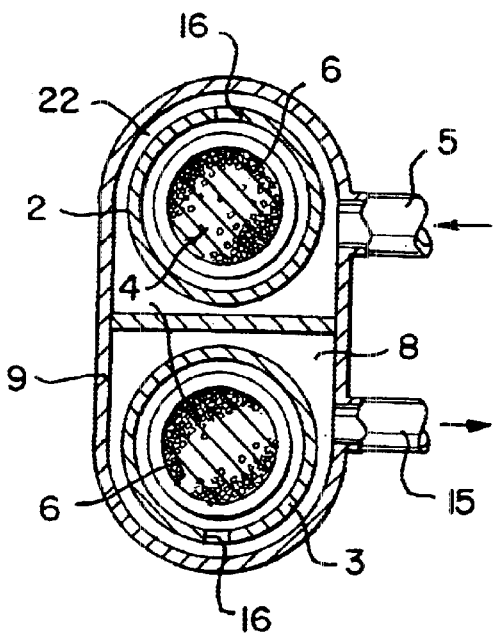
FIG. 1B is a cross-sectional view taken along section line 1B—1B of of FIG. 1A.

Referring now to FIGS. 1A–2B, wherein similar or identical elements are numbered in like manner, a first embodiment for a redundant filtration assembly 1 is presented in FIGS. 1A and 1B. The assembly 1 is provided in two separate stages, with the first stage containing a first casing 2 and the second stage containing a second casing 3 which cooperate to perform redundant filtration of a fluid, for example, a dialysate. First casing 2 includes an inlet port 5 for receiving the fluid prior to filtration. Second casing 3 includes an outlet port 15 for expelling the dual-filtered fluid or infusate, preferably for online infusion to a patient. Inlet port 5 and outlet port 15 may be any standard connector used with dialyzing devices and the like, such as a luer.

First casing 2 and second casing 3 are preferably cylindrical housings, but may be provided in any useful shape. As one of ordinary skill in the art will appreciate, each casing 2, 3 may be similar to a standard dialyzer cartridge of the prior art with an internal extension 24 and potting/dialysate infusion ports 16 which may feed fluid and/or resin into the space 6 around the filter 4. Accordingly, the casings 2, 3 may be manufactured separately with existing dialyzer manufacturing equipment prior to final assembly or, alternatively, may be manufactured together as a single unit.

The filter 4 is preferably a cylindrical bundle of longitudinal semi-permeable hollow fibers 14 or other membrane suitable for endotoxin filtration and the like. Accordingly, the filter membrane 14 may demonstrate a high water permeability and low molecular weight cut-off (e.g. small pore size) in order to accomplish efficient endotoxin removal. However, the filter 4 may be any type of filter suitable for filtering fluids for infusion. The filters 4 are sealed into the casings 2, 3 using a potting compound 8 such as polyurethane, epoxy or other thermosetting material. Furthermore, on an end of casings 2, 3 which is substantially opposite the inlet port 5 or outlet port 15, the internal extension 24 of each casing 2, 3 may be sealed into the potting compound 8 in order to minimize dead flow areas of filtrate.

A plurality of potting ports 16 may be provided as part of casings 2, 3 for injecting the potting compound 8 prior to affixing the casings 2, 3 together. The plurality of potting ports 16 may be configured similarly to dialysate ports found on conventional dialyzers for receiving the injection of the potting compound 8. Standard potting techniques and equipment, such as centrifugal potting used with standard dialyzers, may be used, as can any other techniques which are readily available to one of ordinary skill in the art. Once the excess potting compound 8 is trimmed off and the fiber lumens of filter 4 are opened, two distinct fluid compartments are created in each casing 2, 3.

Stage connectors 9, 10 are further provided at one or both ends of the filtration assembly 1 to seal off the two fluid compartments from each other as well as the external environment. The stage connectors 9, 10 are operative to secure the casings 2, 3 together and are further operative to provide interstage header spaces 7 at, preferably, both ends of the assembly 1 so that fluid communication between the two casings 2, 3 is provided, as described further hereinbelow. Furthermore, the stage connectors 9, 10 may include an inlet port 5 or an outlet port 15 which may be in fluid communication with external spaces 22. The space 22 may lead to the plurality of potting ports 16 and then to an outer portion of the filters 4. Stage connectors 9, 10 may be circumferentially welded or bonded to each casing 2, 3 during manufacture of the assembly 1. The bonding or welding preferably occurs at points 18, 19, 20 and 21. The bonds 19, 21 preferably seal off the interstage header spaces 7 from the external environment. Bonds 18, 20 to the external flange 29 and the casings 2, 3 preferably seal off the filtrate spaces 22 from both the external environment and from each other so as to prevent cross-flow between the casings 2, 3.

Stage connectors 9, 10 may be mated with an interstage header 11 at a mating area 17 to provide an enclosure for the interstage header space 7. The mated portion between the stage connectors 9, 10 and the interstage header 11 may be provided with a seal 12, such as an o-ring, so as to prevent fluid communication between the interstage header space 7 and the outside environment.

The interstage header 11 may further be provided with an entrance port 13. The entrance port 13 is preferably configured as a standard twist lock connector, such as those found on current dialyzer devices. However, any useful connection type is contemplated. The entrance port 13 is further operative so that the filtration assembly 1 may be connected to dialyzer reuse machines, may be integrity tested, and may be disinfected via the entrance port 13 after it has been used.

In a preferred embodiment, the entrance port 13 is capped during normal operation of the filtration assembly 1 so that there is no fluid communication between the interstage header space 7 and the outside environment. It is further contemplated that, in one embodiment, the stage connector 9, the interstage header 11 and the entrance port 13 may be provided as one component rather than an assembly of separate components.

An illustrative example of the normal operation of the filtration assembly 1 of FIGS. 1A and 1B will now be provided. After manufacture of the assembly 1, the device may be connected between a dialysis machine, such as a dialyzer, and an IV infusion set connected to a patient. The dialysis machine is connected to the filtration assembly 1 such that a pressure gradient between the inlet port 5 and the outlet port 15 is established. A filtrate, such as non-sterile substitution fluid, is supplied to the filtration assembly 1 via a tubing (not shown) connected to the inlet port 5.

From the inlet port 5, the filtrate enters the space 6 around the first filter 4 in the casing 2. The potting compound 8 prevents the filtrate from directly entering the interstage header space 7 without first being filtered through the first filter 4. The potting compound 8 preferably seals the potting port 16 and the space 23 on one end such that filtrate may not flow there as well. The filtrate may enter the lumens of the hollow fibers 14 through one or more pores in the outer portion of the filter 4. As stated previously, the bundle of semi-permeable hollow fibers 14 remove endotoxins and the like from the filtrate. The filtrate then exits the first filter 4 through either or both filter ends (or stage outlets) and enters the enclosed interstage header space 7.

The pressure gradient across the assembly 1 then forces the filtrate from the interstage header space 7 into the lumens 14 of the second filter 4 in second casing 3 through the end or stage inlet of the second stage. The potting compound 8 prevents the filtrate from entering the space 6 around the fibers 14 directly from the interstage header space 7 without first entering the fibers 14. The second filter 4 then performs redundant filtration of the filtrate. The filtrate exits the second filter 4 through the potting port 16 of the second filter casing 3 and flows into the space 22 around the second casing 3. Next, the filtrate (now termed infusate) exits the filtration assembly 1 through the outlet port 15. From the outlet port 15, the infusate flows through a tube (not shown) to the IV infusion set attached to a patient.

In this manner, redundant filtration by the first and second filters 4 decreases the likelihood that a single filter failure will allow endotoxins and the like to flow directly into a patient's bloodstream.

Figure 2C:
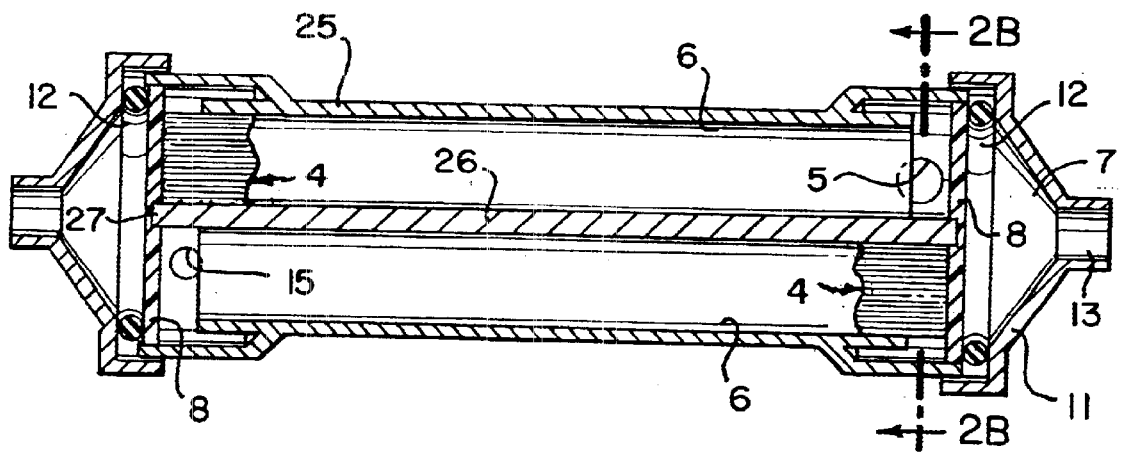
FIG. 2C is a cross-sectional side view of the second filtration assembly of FIG. 2A.
Figure 2B:
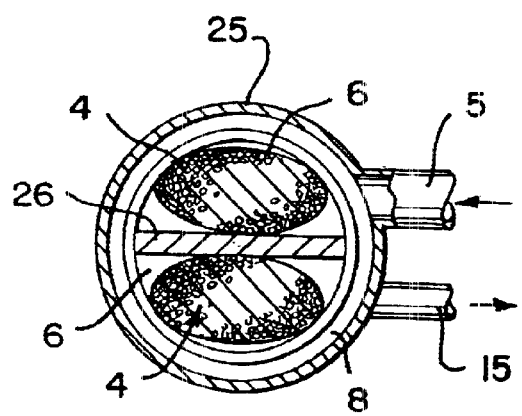
FIG. 2B is a cross-sectional view taken along section line 2B—2B of FIG. 2A.

Referring now to FIGS. 2A–2C, a second embodiment of a redundant filtration assembly 28 is presented which is similar in many details to the first embodiment depicted in FIGS. 1A–1B. Rather than manufacturing separate casings which are later attached, however, the filtration assembly 28 may be constructed from a single large casing 25 which is preferably cylindrical. The large casing 25 is further divided into two longitudinal sections by a separating rib 26. The two longitudinal sections are preferably of equal volumes. The first subdivision of the large casing 25 comprises an inlet port 5 for accepting a filtrate. The second subdivision of the large casing 25 comprises an outlet port 15 for expelling the infusate from the assembly 28 which in turn may be used for direct infusion to a patient.

Each subdivision of the large casing 25 may accommodate a filter 4 which is preferably a longitudinal bundle of semipermeable hollow fibers 14. In this second embodiment which preferably includes a substantially cylindrical, large casing 25, it is contemplated that each filter 4 is ovoid to accommodate the shape of the subdivided large casing 25, as depicted in FIG. 2B. However, each filter 4 may be any other useful shape. Similar to the description of the filtration assembly 1, in the filtration assembly 28 a space 6 is provided between an outer wall of the large casing 25 and each filter 4 to accommodate fluid flow before and after filtration.

Since the large casing 25 is preferably of a unitary construction, the interstage connectors 9, 10 shown for the filtration assembly 1 may not be needed for the filtration assembly 28. Instead, the interstage header 11 is preferably mated to one or both ends of the large casing 25. An o-ring 12 or the like may be used to seal the mated portions of the interstage header 11 and the large casing 25. The interstage header 11 may further include an entrance port 13 with functionality as described with regard to the filtration assembly 1. An interstage header space 7 allows for fluid communication between the filters 4 of both subdivided sections of the large casing 25.

The subdivided portions of the large casing 25 may be sealed from both the outside environment and the interstage header space 7 by a potting compound 8. The potting compound 8 may be injected into the large casing 25 upon manufacture of the the assembly 14 through the inlet port 5 and the outlet port 15, as in conventional dialyzers. Alternatively, the potting compound 8 may be injected by separate potting ports (not shown) as described with regard to the filtration assembly 1. The potting compound 8 is preferably injected such that an end 27 of the separating rib 26 is sealed within the compound 8 and the fluid may only flow to or from each subdivided section through the respective filter 4.

When constructed as described in the foregoing, the operation of the filtration assembly 28 is similar to the exemplary illustration provided for the filtration assembly 1. Although the invention has been described in detail in the foregoing embodiments, it is to be understood that these examples have been provided for purpose of illustration only and that other variations both in form and detail can be made thereupon by those skilled in the art without departing from the spirit and scope of the invention, which is defined solely by the appended claims.

We claim:

1. A filtration assembly, comprising:

a first casing defining a first sterilization stage, the first casing including an inlet port for receiving a first fluid to be filtered, at least one first stage outlet and a first filter membrane, the first fluid being filtered by being conducted across the first filter membrane to produce a first permeate fluid that is discharged through the first stage outlet;

a second casing defining a second sterilization stage, the second casing including an outlet port for discharging a second permeate fluid from the second casing after filtration, the second casing having at least one second stage inlet for receiving the first permeate fluid and a second filter membrane, the first permeate fluid being filtered by being conducted across the second filter membrane to produce the second permeate fluid;

an interstage connector coupled to the first and second casings and allowing communication of the first permeate fluid between the first stage outlet and the second stage inlet; and wherein the first and second casings are arranged so as to prevent the first permeate fluid from directly communicating between the first and second sterilization stages without flowing through the interstage connector.

2. The filtration assembly of claim 1 wherein the first and second stages are disposed substantially parallel to each other.

3. The filtration assembly of claim 1, wherein the first fluid is communicated between the inlet port and the first stage outlet by being conducted across the first filter membrane into a lumen section thereof.

4. The filtration assembly of claim 1, wherein the first permeate fluid is communicated between the second stage inlet and the outlet port by being conducted across the second filter membrane from a lumen section thereof to an extra-luminal space.

5. The filtration assembly of claim 1, further comprising a potting compound inserted between the first filter membrane and the first casing, and inserted between the second filter membrane and the second casing, whereby the fluid is prevented from directly communicating between the first casing and second casing and the interstage connector by the potting compound.

6. The filtration assembly of claim 1, wherein the first and second casings are affixed together.

7. The filtration assembly of claim 1, wherein the interstage connector includes an interstage header operatively connected to another portion of the interstage connector, the interstage header further comprising:

a port for one of receiving and discharging at least one of a second fluid and air.

8. The filtration assembly of claim 7, wherein the port is adapted to be capped during operation of the filtration assembly.

9. The filtration assembly of claim 7, wherein the port is connected to a disinfecting solution for substantially disinfecting the filtration assembly.

10. The filtration assembly of claim 7, further comprising:
a seal for sealing a connection between the interstage header and the other portion of the interstage connector.

11. The filtration assembly of claim 10, wherein the seal is an o-ring.

12. The filtration assembly of claim 1, wherein at least one of the first and second filter membranes are operative to remove endotoxin and bacteria from the first fluid and the first permeate fluid, respectively, prior to the second permeate fluid exiting the outlet port, thereby providing sterile infusion fluid.

13. The filtration assembly of claim 12, wherein at least one of the first and second filter membranes comprise a semipermeable bundle of hollow fibers.

14. The filtration assembly of claim 1, wherein at least one of the first and second casings are substantially cylindrical.

15. The filtration assembly of claim 14, wherein at least one of the first and second filter membranes are substantially cylindrical.

16. The filtration assembly of claim 1, wherein the first stage outlet is at an end of the first casing.

17. The filtration assembly of claim 1, wherein the second stage inlet is at an end of the second casing.

18. A method for filtering a fluid, comprising:
receiving a first fluid to be filtered at an inlet port of a first casing of a filtration assembly;
filtering the first fluid through an outer portion of a first filter in communication with the inlet port and disposing within the first casing, the first fluid being conducted across the filter into a lumen section thereof as a first permeate fluid;
discharging the first permeate fluid through an end of the first filter to an interstage connector;
receiving the first permeate fluid from the interstage connector at an end of a second filter disposed within a second casing of the filtration assembly, the first permeate fluid being received in a lumen section of the second filter;
filtering the first permeate fluid from the lumen section of the second filter to an extra-luminal space as a twice filtered permeate fluid; and
discharging the twice filtered permeate fluid through an outlet port of the second casing.

19. A filtration assembly, comprising:
a casing;
a separating rib for dividing the casing into a first portion for enclosing a first filter and a second portion for enclosing a second filter, the separating rib further for preventing direct fluid communication between the first and second portions;
an inlet port in fluid communication with the first filter for receiving a first fluid to be sterilized by being conducted across the first filter to produce a first permeate fluid;
an outlet port in fluid communication with the second filter for discharging twice filtered permeate fluid; and
at least one interstage portion for providing fluid communication between a first end of the first filter which is adapted to discharge the first permeate fluid and a second end of the second filter which is adapted to receive the first permeate fluid from the first portion so that the first permeate fluid can be conducted across the second filter to produce the twice filtered permeate fluid.

20. The filtration assembly of claim 19, further comprising:
a potting compound disposed between the first filter and the casing for preventing direct fluid communication between the casing and the at least one interstage portion.

21. The filtration assembly of claim 19, wherein the at least one interstage portion comprises an entrance port for receiving at least one of disinfecting solution and air.

22. The filtration assembly of claim 21, wherein the entrance port is capped during an operation of the filtration assembly.

23. The filtration assembly of claim 19, wherein the at least one interstage portion comprises:
a seal for sealing a connection between the interstage portion and the casing.

24. The filtration assembly of claim 23, wherein the seal comprises an o-ring.

25. The filtration assembly of claim 19, further comprising:
the first filter and the second filter.

26. The filtration assembly of claim 19, wherein at least one of the first and second filters are substantially ovoid.

27. The filtration assembly of claim 19, wherein at least one of the first and second filters are substantially cylindrical.

28. The filtration assembly of claim 19, wherein the casing is substantially cylindrical.

29. The filtration assembly of claim 19, further comprising:
a potting port for receiving a potting compound.

30. A filtration assembly, comprising:
a first casing defining a first sterilization stage, the first casing including an inlet port for receiving a first fluid to be sterilized, at least one first stage outlet and a first filter membrane, the first fluid being filtered by being conducted across the first filter membrane to produce a first permeate fluid;
a second casing defining a second sterilization stage, the second casing including an outlet port for discharging a second permeate fluid after filtration in the second sterilization stage, at least one second stage inlet and a second filter membrane, the first permeate fluid being filtered by being conducted across the second filter membrane; and
an interstage connector in communication with the first and second stages and allowing the first permeate fluid to flow between a lumen section of the first filter membrane and a lumen section of the second filter membrane, wherein the first and second sterilization stages are separated so that the first permeate fluid cannot freely communicate between the first and second sterilization stages without flowing through the interstage connector.

31. The filtration assembly of claim 30, wherein the inlet port is formed so that the fluid flows into the first sterilization stage outside of the first filter membrane, the fluid being filtered by conduction across the first filter membrane into the lumen section of the first filter membrane.

32. The filtration assembly of claim 30, wherein the outlet port is formed exterior to the second filter membrane so that the fluid flows through the outlet port by being conducted across the second filter membrane from the lumen section of the second filter membrane.

33. The filtration assembly of claim 30, wherein the first sterilization stage is independent from the second sterilization stage such that the second sterilization stage is a redundant sterilization stage with the fluid being completely filtered in each of the stages.

34. The filtration assembly of claim 30, further comprising:
- a first potting compound inserted between the first filter membrane and the first casing and a second potting compound inserted between the second filter membrane and the second casing, whereby concentrate fluid is prevented from directly communicating between the first casing and second casing and the interstage connector by the potting compound.

35. A method for filtering a fluid, comprising:
- receiving a fluid at an inlet port of a casing of a filtration assembly;
- filtering the fluid by conducting the fluid across a first filter which is in fluid communication with the inlet port and disposed within the casing;
- discharging the fluid through an end of the first filter into an interstage connector;
- receiving the fluid from the interstage connector at an end of a second filter disposed within the casing;
- filtering the fluid by conducting the fluid across the second filter, wherein the fluid is conducted in a first direction across the first filter and in a second direction across the second filter; and
- discharging the fluid through an outlet port of the casing which is in fluid communication with the second filter.

36. The method of claim 35, wherein the first direction is from a first extra-luminal space to a lumen location of the first filter and the second direction is from a lumen section of the second filter to a second extra-luminal space.

37. The method of claim 35, further comprising:
- disposing a member between the first and second filters to prevent direct fluid flow between the first and second filters, the fluid having to flow through the interstage connector to flow between the first and second filters.

* * * * *